(12) United States Patent
Firmin et al.

(10) Patent No.: US 6,210,439 B1
(45) Date of Patent: Apr. 3, 2001

(54) TO SUBCUTANEOUS PROSTHESES FOR MAMMAPLASTY

(75) Inventors: Francoise Firmin, Paris; Axel Arnaud, Neuilly-sur-Seine, both of (FR)

(73) Assignee: Ethicon S.A.S (FR)

( * ) Notice: Subject to any disclaimer, the term of this patent is extended or adjusted under 35 U.S.C. 154(b) by 0 days.

(21) Appl. No.: 09/412,478

(22) Filed: Oct. 5, 1999

Related U.S. Application Data

(63) Continuation of application No. 09/059,910, filed on Apr. 14, 1998, now abandoned.

(30) Foreign Application Priority Data

Apr. 17, 1997 (FR) .................................................. 97 04752

(51) Int. Cl.$^7$ ...................................................... A61F 2/12
(52) U.S. Cl. ................................................. 623/8; 606/151
(58) Field of Search .................................. 623/8; 606/151

(56) References Cited

U.S. PATENT DOCUMENTS

| | | | |
|---|---|---|---|
| 4,840,629 | 6/1989 | Bustos | 623/8 |
| 5,258,000 | 11/1993 | Gianturco | 606/151 |
| 5,397,331 | * 3/1995 | Himpens et al. | 606/151 |
| 5,451,235 | 9/1995 | Lock et al. | 606/213 |
| 5,584,884 | * 12/1996 | Pignataro | 623/8 |
| 5,634,931 | 6/1997 | Kugel | 606/151 |

FOREIGN PATENT DOCUMENTS

| | | | |
|---|---|---|---|
| 0 322 194 A1 | 12/1988 | (EP) . | |
| 1035202 | 4/1951 | (FR) | 19/1 |
| 2682284 | 10/1991 | (FR) | A61F/2/12 |

OTHER PUBLICATIONS

Author Unknown, "Analysis Of Surgical Principles," *Plastic Surgery For Mammary Hypertrophy And Ptosis*, pp. 46–68.

Author Unknown, "Periareolar Technique," *Mammary Ptosis*, Chapter VI, pp. 59–65.

Germain Gillet, "Mammary Suspension By Sub–cutaneous Prosthesis," *Notes On Surgical Technique*, Oct. 4, 1952, p. 1325.

\* cited by examiner

*Primary Examiner*—Bruce Snow

(57) ABSTRACT

A subcutaneous prosthesis for mammaplasty repair comprising a netting having a generally circular shape with a V shaped opening extending from its center. The prosthesis having a metallic reinforcing wire that extends around the periphery of the circular netting. The ends of the reinforcing wire being maintained in position by a blocking piece. When the prosthesis is deployed, by tightening the reinforcing wire the prosthesis can be formed into a conical shape suitable for mammary repair.

8 Claims, 2 Drawing Sheets

TO SUBCUTANEOUS PROSTHESES FOR MAMMAPLASTY

This is a Continuation of prior application No. 09/059,910, filed Apr. 14, 1998, now abandoned.

The present invention relates to subcutaneous prostheses for mammaplasty.

BACKGROUND OF THE INVENTION

It is known in breast surgery to use internal lattices configured as bonnets in order to constitute supports for holding the glandular mass and to afford a certain stability to the reshaped breasts.

In particular, Dr Firmin, taking up a technique proposed as early as 1952 by Dr Germain Gillet in his publication: "Mammary suspension by subcutaneous prosthesis"—Notes on surgical techniques under the direction of L. LEGER-1952-60-No. 62-page 325, presented—at the VIth video forum on plastic and cosmetic surgery, organized by the SOF.C.P.R.E, and held on 24th and 25th June 1994 in Toulouse—a mammaplasty technique by the areolar route, utilizing such an internal support system.

More precisely, the subcutaneous prosthesis presented at this conference by Dr Firmin consisted of a lattice made of VICRYL (trademark) having a mainly circular general shape, cut with a central hole and a V-shaped opening extending from its centre.

A metal reinforcement, closed upon itself, was passed through the meshes of this lattice so as to encircle it near its periphery.

Such an assembly consisting of a lattice and a metal reinforcement is used in the following way.

By drawing this reinforcement tight, the surgeon gives the lattice the shape and the desired dimensions for the bonnet. He places this bonnet on the reshaped glandular mass and sutures the lattice to the pectoral muscle. This latter manoeuvre is greatly facilitated by the reinforcement, since the latter holds the lattice in place throughout this operation.

Once the lattice has been fixed, the surgeon removes the reinforcement by sliding it through the meshes.

However, the lattice/reinforcement assembly which was presented by Dr Firmin at this conference is not entirely satisfactory in terms of its manipulation.

In particular, in order to keep the reinforcement looped on itself, the surgeon had to proceed by twisting the ends of the said reinforcement on one another; and once the lattice was in place, he had to untwist these ends in order to remove the metal reinforcement. As will be readily appreciated, this manoeuvre was particularly awkward and represented a potential source of injury to the patient.

It is therefore an object of the invention to remedy this disadvantage.

SUMMARY OF THE INVENTION

To this end, the invention provides an assembly which includes a netting intended to constitute a subcutaneous prosthesis for mammaplasty, and a metal reinforcement in the form of an open loop which extends near the periphery of the said netting and is intended to be drawn tight in order to confer on the said netting a bonnet shape, characterized in that it includes a blocking piece by means of which it is possible to hold the two ends of the metal reinforcement relative to one another.

In particular, the blocking piece is advantageously a piece made of plastic with two channels in which the ends of the reinforcement are blocked by friction, while being able to be slid in the said channels under the effect of a force exerted by an operator.

Other characteristics and advantages of the invention will become evident from the description which follows. This description is purely illustrative and nonlimiting. It should be read with reference to the attached drawings, in which:

DETAILED DESCRIPTION OF THE INVENTION

Figure 1:
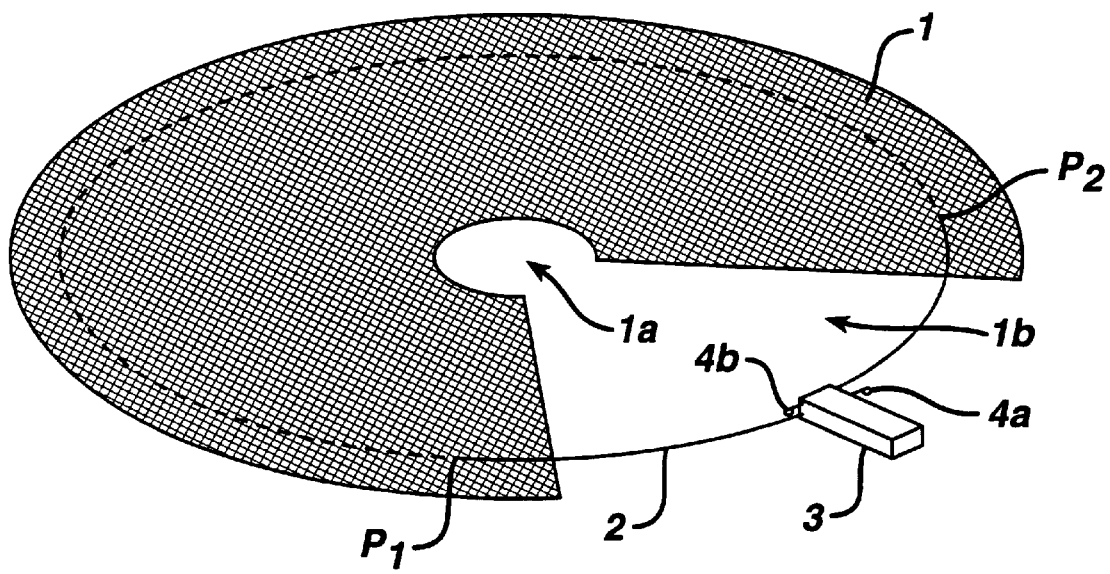
FIGS. 1 and 2 are two perspective representations of a device according to one possible embodiment of the invention.
Figure 2:
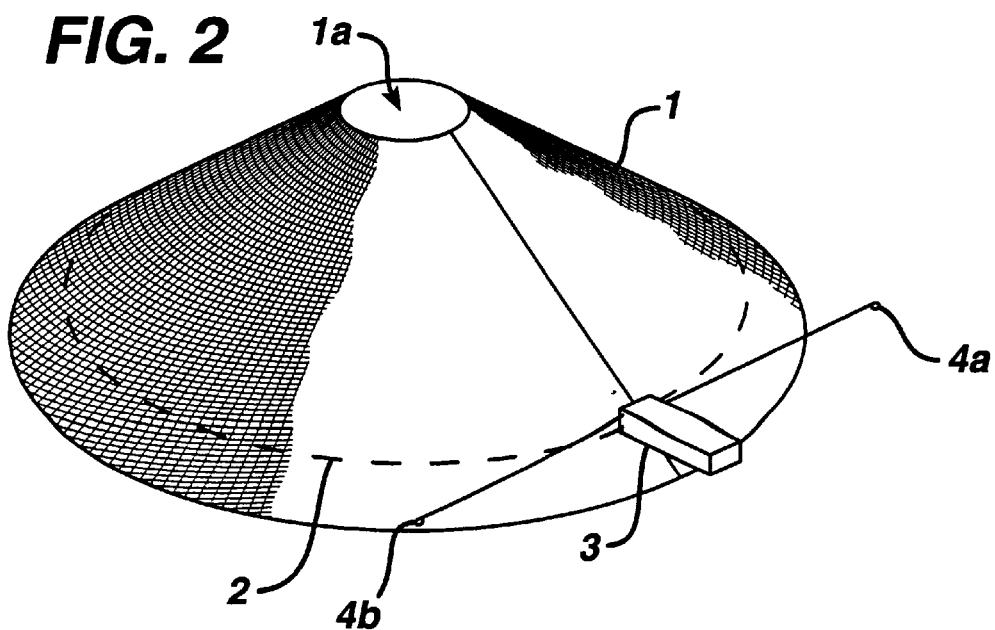

The assembly illustrated in FIGS. 1 and 2 includes a lattice 1 and a reinforcement 2.

The lattice 1 is cut out with a general circular shape. It has a central hole 1a, as well as an opening 1b which extends in a V shape from its centre.

The metal reinforcement 2 is a metal wire in the form of an open loop which runs round the lattice 1 near its periphery.

In the example illustrated in FIGS. 1 and 2, the said reinforcement 2 is fixed to the lattice 1 by being threaded through the meshes thereof so as to be passed alternately on either side of the said lattice 1.

The two ends of this reinforcement 2 are held relative to one another by way of a blocking piece 3.

This blocking piece 3 is in this case a parallelepipedal tongue of plastic which has, near one of its end edges, two continuous parallel channels through which the ends of the reinforcement 2 are passed.

These channels are of such a diameter that the said ends are blocked by friction against the walls of the said channels under the tightening effect afforded by the elastic return of the said reinforcement 2 to its deployed position, while being able to be slid in the said channels under the effect of a force exerted by an operator.

Thus, by exerting a simple force pulling or pushing back the ends of the reinforcement 2 relative to the blocking tongue, the surgeon regulates the diameter of the reinforcement 2 and the dimension of the bonnet which the said lattice 1 defines when the reinforcement 2 is drawn tight.

Furthermore, the ends of the reinforcement 2 emerging beyond the channels are folded back on themselves in loops 4a, 4b by means of which it is possible to avoid catching of the edges on the said reinforcement ends.

Once the bonnet is in place on the glandular mass and the lattice 1 has been sutured to the pectoral muscle, the surgeon straightens out one of the loops 4a, 4b of the reinforcement 2, then pulls on the said reinforcement 2 in order to slide it relative to the lattice 1.

To give an example of the dimensions, the lattice 1 can have an initial diameter of 120 mm, its central hole being 20 mm, the V-shaped opening extending over a sector corresponding to an angle of 80°.

The metal reinforcement 2 is passed through this lattice 1 in such a way as to define, when it is not drawn tight and when the lattice is deployed flat, a circle of 32 mm in diameter.

This reinforcement 2 consists of a metal wire with a cross-section of 0.8 mm in diameter.

The points $P_1$ and $P_2$ where the reinforcement 2 opens out from the lattice 1 near the V-shaped opening thereof are separated angularly by 12.5° in relation to the edges of the said V-shaped opening.

The lattice 1 is, for example, made of VICRYL (trademark), a composite consisting of terephthalic polyester (40%) and polyglactin 910 (60%) filaments, which composite is absorbed by hydrolysis within approximately 90 days.

The blocking tongue 3 has a length of 3 cm, a thickness of 0.5 cm.

The two channels which pass through this tongue 3 are separated by 2.5 mm.

This tongue 3 is, for example, made by casting polypropylene.

Other alternative embodiments of the invention are of course possible.

Figure 3:
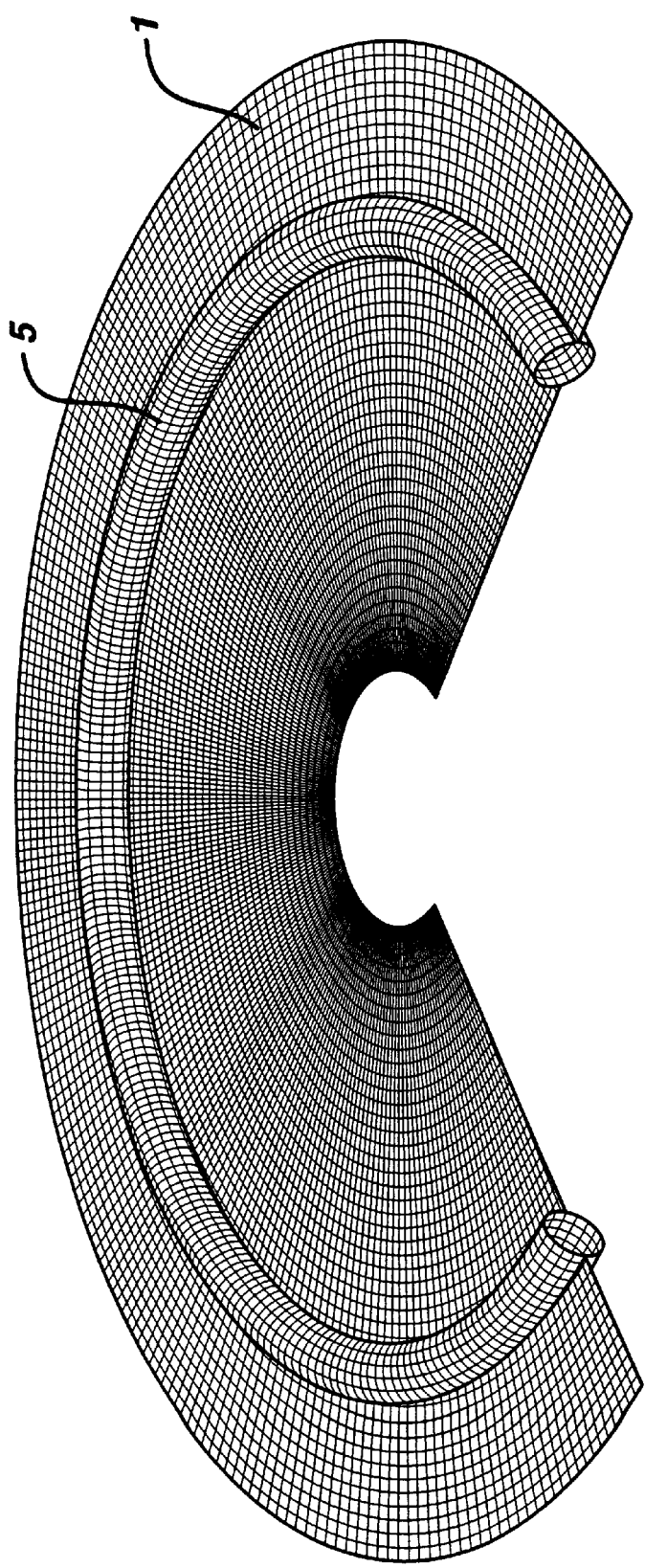
FIG. 3 is a perspective representation illustrating an alternative lattice also possible for a device according to another embodiment of the invention.

In particular, as has been illustrated in FIG. 3, the lattice 1 advantageously has a channel 5 through which the reinforcement 2 is passed, instead of being threaded through the meshes of the said lattice.

What is claimed is:

1. A subcutaneous prosthesis for mammaplasty comprising a netting having a generally circular shape with a central opening and a V-shaped wedge opening extend from said central opening, the circular netting having a periphery with a reinforcing element extending around the circular netting near the periphery and attached to the netting about the periphery, and a blocking piece in communication with the reinforcing piece, wherein when the reinforcing element is tightened the netting will assume a bonnet shape.

2. The subcutaneous prosthesis of claim 1 wherein the reinforcing element is a wire having two ends that are secured by the blocking piece.

3. The subcutaneous prosthesis of claim 2 wherein the blocking piece has channels therein to engage the ends of the reinforcing element.

4. The subcutaneous prosthesis of claim 1 wherein the netting is a lattice made from at least one partially absorbable material.

5. The subcutaneous prosthesis of claim 1 wherein the V-shaped opening extends over an angular sector of about 80°.

6. The subcutaneous prosthesis of claim 1 wherein the netting has a channel about the periphery through which the reinforcing element is passed.

7. The subcutaneous prosthesis of claim 1 wherein the netting comprises a plurality of fibers and the reinforcing element is attached to the periphery of the netting by inserting the reinforcing elements through the fibers of the netting about the periphery.

8. The subcutaneous prosthesis of claim 1 wherein the reinforcing element is a metallic wire.

* * * * *